United States Patent [19]
Lin et al.

[11] Patent Number: 6,107,521
[45] Date of Patent: Aug. 22, 2000

[54] PROCESS FOR THE PREPARATION OF SECONDARY AMINES

[75] Inventors: Sue L. Lin, Levittown, Pa.; Weixia M. Zhou, Middlesex; George W. Matcham, Flemington, both of N.J.

[73] Assignee: Celgro, North Brunswick, N.J.

[21] Appl. No.: 09/460,560

[22] Filed: Dec. 14, 1999

[51] Int. Cl.[7] .................................................. C07C 209/00
[52] U.S. Cl. ............................................. 564/395; 564/405
[58] Field of Search ..................................... 564/395, 405, 564/404

[56] References Cited

U.S. PATENT DOCUMENTS

| 4,757,144 | 7/1988 | Okabe et al. | 544/404 |
| 4,792,622 | 12/1988 | Yokota et al. | 564/398 |

*Primary Examiner*—Samuel Barts
*Attorney, Agent, or Firm*—Mathews, Collins, Shepherd & Gould, P.A.

[57] ABSTRACT

N,N-disubstituted amines in which the amino nitrogen atom is bound to the carbon atom of an aromatic ring disubstituted in the positions ortho to the carbon atom, are prepared by allowing a primary amine and a compound in which an ortho, ortho-disubstituted aromatic compound carrying a nucleofuge substituent, to react in a basic environment in the presence of a catalytic palladium(0) complex and a ligand, the ratio of palladium complex to ligand being greater than at least 1:1. A typical embodiment involves the reaction of 2-methyl-6-ethylphenyl-trifluoromethylsulfonate and (S)-1-methoxy-2-aminopropane in the presence of bis (dibenzylideneacetone)palladium, tri-tert.-butylphosphine, and sodium tert.-butoxide to yield (S)-N-(1-methoxyprop-2-yl)-2-methyl-6-ethylphenylamine.

19 Claims, No Drawings

PROCESS FOR THE PREPARATION OF SECONDARY AMINES

The present invention pertains to an intermolecular process for the preparation of secondary and tertiary amines having at least one ortho, ortho disubstituted aromatic substituent.

Conventional methods of preparing secondary and tertiary amines generally produce less than optimum results when one of the amine substituents is an aromatic group which itself is substituted, particularly an aromatic group having one or more electron donating groups. Significant improvement is possible utilizing palladium catalyzed amination of aryl halides in which an amine is allowed to react with an aryl halide such as bromobenzene, o- and p-bromotoluenes, p-methoxybromobenzene, and the like, in the presence of a palladium(0) complex and a ligand such as tri-(tert.-butyl)phosphine. See, e.g., Hartwig, et al., *J. Org. Chem.* 1999, 64, 5575; Hartwig, *Synlett.* 1997 329; Hartwig, *Angew. Chem. Int. Ed.* 1998, 37, 2048; Ukai, et al., *J. Organomet. Chem.* 1974, 85, 253; Nishiyama, et al., *Tetrahedron Lett.* 1998, 39, 617; Hamann, et al., *J. Am. Chem. Soc.* 1998, 120, 3694; and Driver, et al., *J. Am. Chem. Soc.* 1996, 118, 7217.

Notwithstanding these improvements, difficulties remain for the preparation of secondary and tertiary amines in which in one of the substituents on the amino nitrogen atom is an ortho, ortho disubstituted aromatic group. In such circumstances the reaction is sluggish with poor yields (e.g., ~30%) even with conventional Hartwig conditions. Alternative routes such as reductive amination may require specialized catalysts. The matter is further complicated if the maintenance of chirality on an amino substituent is required.

The present invention provides a process for the preparation of N,N-disubstituted and N,N,N-trisubstituted amines in which the amino nitrogen atom is bound to a carbon atom of an aromatic ring substituted in both ortho positions. The process involves allowing a primary or secondary amine and an aromatic compound carrying a nucleofuge and ortho, ortho-disubstitution to react in a basic environment in the presence of a catalytic palladium(0) or nickel complex and a ligand to produce the corresponding secondary or tertiary amine.

The ratio of palladium(0) or nickel complex to ligand is greater than at least 1:1, typically at least 2:1, preferably at least 4:1, and can be as high as 10:1. These higher ratios permit milder conditions and lead to improved results in terms of higher conversions.

Typical nucleofuges include the iodo, bromo, chloro, methanesulfonato, and trifluoromethanesulfonato radicals with trifluoromethanesulfonato, bromo, and iodo being preferred. The aromatic compound is disubstituted by the same or different groups in the positions ortho to the nucleofuge substituent. The ortho substituents can be alkyl, alkoxy, haloalkyl, alkoxyalkyl, etc. Typical aromatic reactants include 2,6-dimethylphenyl bromide, 2,6-dimethylphenyl chloride, 2,6-dimethylphenyl iodide, 2,6-dimethylphenylmethylsulfonate, 2,6-dimethylphenyltrifluoromethylsulfonate, 2-methyl-6-ethylphenyl bromide, 2-methyl-6-ethylphenyl chloride, 2-methyl-6-ethylphenyl iodide, 2-methyl-6-ethylphenylmethylsulfonate, 2-methyl-6-ethylphenyltrifluoromethylsulfonate, 2,6-diethylphenyl bromide, 2,6-diethylphenyl chloride, 2,6-diethylphenyl iodide, 2,6-diethylphenylmethylsulfonate, and 2,6-diethylphenyltrifluoromethylsulfonate.

The primary or secondary amine can be an unsubstituted or substituted N-alkylamine, N,N-dialkylamine, N-arylamine, N-alkyl-N-arylamine, N-arylalkylamine, N,N-di(arylalkyl)amine, N-alkyl-N-arylalkylamine, or N,N-diarylamine, as for example methylamine, ethylamine, propylamine, methoxypropylamine, butylamine, phenethylamine, aniline, dimethylamine, ethylmethylamine, and the like. If the unsubstituted or substituted amine is chiral, as for example (R)- or (S)-1-methoxy-2-aminopropane, such chirality advantageously is maintained in the course of the reaction.

Suitable palladium and nickel catalysts include palladium chloride, palladium acetate, bis(trans,trans-dibenzylideneacetone)palladium, [1,1'-bis(diphenylphosphino)ferrocene]dichloropalladium, bis(triphenylphosphino)dichloropalladium, tetrakis(triphenylphosphine)palladium, bis(triphenylphosphino)dichloronickel, nickelcarbonyl, bis(1,5-cyclooctadiene)nickel, and the like. Suitable ligands include tri-(tert.-butyl)phosphine, 1,1'-bis(diphenylphosphino)ferrocene, 2,2'-bis(diphenylphosphino)-1,1'-binaphthyl, tri-(o-tolyl)phosphine, 4,12-bis(diphenylphosphanyl)[2.2]paracyclophane, 1,1'-bis(di-p-methoxyphenylphosphino)ferrocene, 1,1'-bis(di-p-trifluoromethylphenylphosphino)ferrocene, 1,1'-bis(ditolylphosphino)ferrocene, 2,2'-bis(diphenylphosphino)diphenyl ether, and the like.

Although heat can be applied, advantageously the reaction can be conducted at ambient temperatures; e.g., ~20 to 30° C. When heat is utilized, typically the temperatures need be no greater than about 130° C.

Suitable bases include lutidine, sodium butoxide, potassium carbonate, cesium carbonate, tert.-butyl lithium, potassium phosphate, triethylamine with potassium carbonate, and the like. Preferably the reaction is conducted in an inert organic solvent, as for example aromatic hydrocarbons such as benzene and toluene and ethers such as dioxane and the like. Isolation is straightforward and presents no problems.

When a secondary amine if obtained, it can be further reacted yielding, for example, a tertiary amide; i.e., acylated with chloroacetyl chloride.

The following examples will serve to further illustrate the nature of the present invention but should not be construed as a limitation on the scope thereof, which scope is defined solely by the appended claims.

EXAMPLE 1

A. To a solution of 1.22 g (10 mmol) of 2,6-dimethylphenol in 50 mL of methylene chloride at 0° C. are added dropwise, under nitrogen and with constant stirring, a solution of 3.10 g (11 mmol) of trifluoromethanesulfonic anhydride in 20 mL of methylene chloride and 2.14 g (20 mmol) of 2,6-lutidine. The temperature is maintained at 0° C. during the addition and reaction (0.5–1 hr) with cooling as necessary. The reaction is monitored with thin layer chromatography. Upon substantial completion of the reaction, 70 mL of ice and water are added and the organic layer separated. The aqueous phase is extracted with methylene chloride (30 mL×2) and the combined methylene chloride layers are washed with saturated sodium chloride solution, dried over anhydrous magnesium sulfate, and concentrated to yield 2,6-dimethylphenyltrifluoromethylsulfonate. In one such run, 2.38 g of product (94%) were obtained.

B. A mixture of 2,6-dimethylphenyltrifluoromethylsulfonate (1.57 mmol), (S)-1methoxy-2-aminopropane (1.58 mmol), bis(dibenzylideneacetone)palladium (0.0312–0.078 mmol), tri-tert.-butylphosphine (0.0078 mmol) and sodium tert.-butoxide (1.88 mmol) is stirred under a nitrogen atmosphere in 2 mL of de-gassed toluene at room temperature (~25° C.). The reaction is monitored with thin layer chromatography. After three hours, the reaction slurry is loaded onto silica gel and purified by flash chromatography with 5–10% ethyl acetate in hexane to yield 90% of (S)-N-(1-methoxyprop-2-yl)-2,6-dimethylphenylamine.

EXAMPLE 2

Utilizing a molar equivalent amount of 2,6-dimethylbromobenzene, a 2% mol percent of bis(dibenzylideneacetone)palladium, and a 4:1 molar ratio of catalyst to ligand (tri-tert-butylphosphine) in the procedure of Example 1B, an 88% yield of N-(1-methoxyprop-2-yl)-2,6-dimethylphenylamine is obtained after 4 hours.

EXAMPLE 3

Utilizing a molar equivalent amount of 2-methyl-6-ethylbromobenzene, a 5% mol percent of bis(dibenzylideneacetone)palladium, and a 10:1 molar ratio of catalyst to ligand (tri-tert-butylphosphine) in the procedure of Example 1B, an 82% yield of N-(1-methoxyprop-2-yl)-2-methyl-6-ethylphenylamine is obtained after 6 hours.

EXAMPLE 4

Utilizing a molar equivalent amount of 2-methyl-6-ethyliodobenzene, a 5% mol percent of bis(dibenzylideneacetone)palladium, and a 10:1 molar ratio of catalyst to ligand (tri-tert-butylphosphine) in the procedure of Example 1B, an 90% yield of N-(1-methoxyprop-2-yl)-2-methyl-6-ethylphenylamine is obtained after 6 hours.

EXAMPLE 5

Utilizing a molar equivalent amount of 2-methyl-6-ethylphenyltrifluoromethylsulfonate, in the procedure of Example 1B, yields (S)-N-(1-methoxyprop-2-yl)-2-methyl-6-ethylphenylamine.

EXAMPLE 6

Following the procedure of Example 1B but substituting molar equivalent amounts of (R,S)-1-methoxy-2-aminopropane, methylamine, ethylamine, propylamine, butylamine, phenethylamine, aniline, there are respectively obtained (R,S)-N-(1-methoxyprop-2-yl)-2,6-dimethylphenylamine, N-methyl-2,6-dimethylphenylamine, N-ethyl-2,6-dimethylphenylamine, N-propyl-2,6-dimethylphenylamine, N-butyl-2,6-dimethylphenylamine, N-phenethyl-2,6-dimethylphenylamine, and N-phenyl-2,6-dimethylphenylamine.

EXAMPLE 7

(S)-N-(1-Methoxyprop-2-yl)-2-methyl-6-ethylphenylamine is acylated with chloroacetyl chloride in a manner known per se to yield the known (S)-N-chloroacetyl-N-(1-methoxyprop-2-yl)-2-methyl-6-ethylphenylamine (also known as S-metolachor).

What is claimed is:

1. A process for the preparation of an N,N-disubstituted or N,N,N-trisubstituted amine in which in one of the substituents the amino nitrogen atom is bound to the carbon atom of an aromatic ring disubstituted in the positions ortho to said carbon atom, which process comprises allowing
   (i) a primary or secondary amine and
   (ii) a compound in which said carbon atom of the ortho, ortho-disubstituted aromatic ring is bound to a nucleofuge, to react in a basic environment in the presence of
   (iii) a catalytic palladium(0) or nickel complex and
   (iv) a ligand in which the ratio of palladium(0) or nickel complex to ligand is greater than at least 1:1.

2. The process according to claim 1 wherein the reaction is conducted in an inert organic solvent.

3. The process according to claim 1 wherein a catalytic palladium(0) complex is employed and the ratio of palladium(0) complex to ligand is at least 4:1.

4. The process according to claim 1 wherein a catalytic palladium(0) complex is employed and the ratio of palladium(0) complex to ligand is at least 4:1.

5. The process according to claim 1 wherein the nucleofuge is the iodo, bromo, chloro, methanesulfonato, or trifluoromethanesulfonato radical.

6. The process according to claim 1 wherein said primary or secondary amine is an unsubstituted or substituted monoalkylamine.

7. The process according to claim 6 wherein said unsubstituted or substituted monoalkylamine is chiral.

8. The process according to claim 6 wherein said unsubstituted or substituted monoalkylamine is 1-methoxy-2-aminopropane.

9. The process according to claim 8 wherein said 1-methoxy-2-aminopropane is (S)-1-methoxy-2-aminopropane.

10. The process according to claim 1 wherein said aromatic ring is disubstituted by the same or different alkyl groups in the ortho positions.

11. The process according to claim 1 wherein the compound in which said carbon atom of the ortho,ortho-disubstituted aromatic ring is bound to a nucleofuge is 2,6-dimethylphenyl bromide, 2,6-dimethylphenyl chloride, 2,6-dimethylphenyl iodide, 2,6-dimethylphenylmethylsulfonate, 2,6-dimethylphenyltrifluoromethylsulfonate, 2-methyl-6-ethylphenyl bromide, 2-methyl-6-ethylphenyl chloride, 2-methyl-6-ethylphenyl iodide, 2-methyl-6-ethylphenylmethylsulfonate, 2-methyl-6-ethylphenyltrifluoromethylsulfonate, 2,6-diethylphenyl bromide, 2,6-diethylphenyl chloride, 2,6-diethylphenyl iodide, 2,6-diethylphenylmethylsulfonate, or 2,6-diethylphenyltrifluoromethylsulfonate.

12. The process according to claim 1 wherein the catalytic palladium(0) or nickel complex is palladium chloride, palladium acetate, bis(trans,trans-dibenzylideneacetone) palladium, [1,1'-bis(diphenylphosphino)ferrocene] dichloropalladium, bis(triphenylphosphino) dichloropalladium, tetrakis(triphenylphosphine)palladium, bis(triphenylphosphino)dichloronickel, nickelcarbonyl, or bis(1,5-cyclooctadiene)nickel.

13. The process according to claim 12 wherein the catalytic palladium(0) or nickel complex is bis(dibenzylideneacetone)palladium or tetrakis (triphenylphosphine)palladium.

14. The process according to claim 1 wherein the ligand is tri-(tert.-butyl)phosphine, 1,1'-bis(diphenylphosphino) ferrocene, 2,2'-bis(diphenylphosphino)-1,1'-binaphthyl, tri-(o-tolyl)phosphine, 4,12-bis(diphenylphosphanyl)-[2.2] paracyclophane, 1,1'-bis(di-p-methoxyphenylphosphino) ferrocene, 1,1'-bis(di-p-trifluoromethylphenylphosphino) ferrocene, 1,1'-bis(ditolylphosphino)ferrocene, or 2,2'-bis (diphenylphosphino)diphenyl ether.

15. A process according to claim 1 for the preparation of N-(1-methoxyprop-2yl)-2,6-dimethylphenylamine which comprises allowing
   (i) 1-methoxy-2-aminopropane and
   (ii) 2,6-dimethylphenyl bromide, 2,6-dimethylphenyl chloride, 2,6-dimethylphenyl iodide, 2,6- dimethylphenylmethylsulfonate, or 2,6-dimethylphenyltrifluoromethylsulfonate, to react in a basic environment in the presence of (iii) palladium(0) or nickel complex catalyst which is palladium chloride, palladium acetate, bis(trans,trans-dibenzylideneacetone)palladium, [1,1'-bis(diphenylphosphino)ferrocene]dichloropalladium, bis(triphenylphosphino)dichloropalladium, tetrakis(triphenylphosphine)palladium, bis(triphenylphosphino)dichloronickel, nickelcarbonyl, or bis(1,5-cyclooctadiene)nickel, and (iv) a ligand which is tri-(tert.-butyl)phosphine, 1,1'-bis(diphenylphosphino)ferrocene, 2,2'-bis(diphenylphosphino)-1,1'-binaphthyl, tri-(o-tolyl)phosphine, 4,12-bis(diphenylphosphanyl)[2.2]paracyclophane, 1,1'-bis(di-p-methoxyphenylphosphino)ferrocene, 1,1'-bis(di-p-trifluoromethylphenylphosphino)ferrocene, 1,1'-bis(ditolylphosphino)ferrocene, or 2,2'-bis(diphenylphosphino)diphenyl ether in which the ratio of palladium(0) complex to ligand is greater than at least 1:1.

16. The process according to claim 15 wherein the catalytic palladium(0) or nickel complex is bis(dibenzylideneacetone)palladium or tetrakis(triphenylphosphine)palladium.

17. A process according to claim 1 for the preparation of N-(1-methoxyprop-2-yl)-2-methyl-6-ethylphenylamine which comprises allowing (i) 1-methoxy-2-aminopropane and (ii) 2-methyl-6-ethylphenyl bromide, 2-methyl-6-ethylphenyl chloride, 2-methyl-6-ethylphenyl iodide, 2-methyl-6-ethylphenylmethylsulfonate, or 2-methyl-6-ethylphenyltrifluoromethylsulfonate, to react in a basic environment in the presence of ((iii) palladium(0) or nickel complex catalyst which is palladium chloride, palladium acetate, bis(trans,trans-dibenzylideneacetone)palladium, [1,1'-bis(diphenylphosphino)ferrocene]dichloropalladium, bis(triphenylphosphino)dichloropalladium, tetrakis(triphenylphosphine)palladium, bis(triphenylphosphino)dichloronickel, nickelcarbonyl, or bis(1,5-cyclooctadiene)nickel, and (iv) a ligand which is tri-(tert.-butyl)phosphine, 1,1'-bis(diphenylphosphino)ferrocene, 2,2'-bis(diphenylphosphino)-1,1'-binaphthyl, tri-(o-tolyl)phosphine, 4,12-bis(diphenylphosphanyl)[2.2]paracyclophane, 1,1'-bis(di-p-methoxyphenylphosphino)ferrocene, 1,1'-bis(di-p-trifluoromethylphenylphosphino)ferrocene, 1,1'-bis(ditolylphosphino)ferrocene, or 2,2'-bis(diphenylphosphino)diphenyl ether in which the ratio of palladium(0) complex to ligand is greater than at least 1:1.

18. The process according to claim 17 wherein the catalytic palladium(0) or nickel complex is bis(dibenzylideneacetone)palladium or tetrakis(triphenylphosphine)palladium.

19. A process according to claim 17 wherein (S)-1-methoxy-2-aminopropane is employed to yield (S)-N-(1-methoxyprop-2-yl)-2-methyl-6-ethylphenylamine.

* * * * *